(12) United States Patent
Aimi et al.

(10) Patent No.: US 7,744,545 B2
(45) Date of Patent: Jun. 29, 2010

(54) GUIDE WIRE

(75) Inventors: Youki Aimi, Fujinomiya (JP); Hideo Satou, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 11/902,863

(22) Filed: Sep. 26, 2007

(65) Prior Publication Data

US 2008/0161727 A1    Jul. 3, 2008

Related U.S. Application Data

(60) Provisional application No. 60/878,663, filed on Jan. 5, 2007.

(30) Foreign Application Priority Data

Dec. 28, 2006  (JP)  ............................. 2006-356642
Jun. 27, 2007  (JP)  ............................. 2007-169347

(51) Int. Cl.
    *A61B 5/00*    (2006.01)
(52) U.S. Cl. ...................................... 600/585
(58) Field of Classification Search ................. 600/585
    See application file for complete search history.

(56) References Cited

U.S. PATENT DOCUMENTS

| | | | |
|---|---|---|---|
| 4,832,047 A | 5/1989 | Sepetka et al. | |
| 4,925,445 A | 5/1990 | Sakamoto et al. | |
| 5,060,660 A | 10/1991 | Gambale et al. | |
| 5,069,226 A | 12/1991 | Yamauchi et al. | |
| 5,147,317 A * | 9/1992 | Shank et al. | 604/164.13 |
| 5,238,004 A | 8/1993 | Sahatjian et al. | |
| 5,269,759 A | 12/1993 | Hernandez et al. | |
| 5,345,945 A | 9/1994 | Hodgson et al. | |
| 5,368,049 A | 11/1994 | Raman et al. | |
| 5,373,619 A | 12/1994 | Fleischhacker et al. | |
| 5,402,799 A | 4/1995 | Colon et al. | |
| 5,411,476 A | 5/1995 | Abrams et al. | |

(Continued)

FOREIGN PATENT DOCUMENTS

EP    1 266 670 A1    12/2002

(Continued)

OTHER PUBLICATIONS

Extended European Search Report issued in corres. EP 07019043.4, Mar. 12, 2008, EPO, Munich, DE.

(Continued)

*Primary Examiner*—Max Hindenburg
*Assistant Examiner*—Sean P Dougherty
(74) *Attorney, Agent, or Firm*—Buchanan Ingersoll & Rooney PC

(57) ABSTRACT

A guide wire includes a wire body having a tapered portion disposed on a distal end portion thereof and having an outside diameter progressively reduced toward a distal end thereof. The guide wire includes a coil disposed in covering relation to the distal end portion of the wire body and a helically shaped wire. The coil includes an increasing wire-diameter portion where the diameter of the wire increases continuously toward a distal end thereof, the increasing wire-diameter portion being disposed in covering relation to the outer circumference of at least a portion of the tapered portion in a longitudinal direction.

23 Claims, 12 Drawing Sheets

U.S. PATENT DOCUMENTS

| | | | |
|---|---|---|---|
| 5,452,726 | A | 9/1995 | Burmeister et al. |
| 5,497,786 | A | 3/1996 | Urick |
| 5,498,250 | A | 3/1996 | Prather |
| 5,772,609 | A | 6/1998 | Nguyen et al. |
| 5,797,857 | A | 8/1998 | Obitsu |
| 5,876,356 | A | 3/1999 | Viera et al. |
| 5,924,998 | A | 7/1999 | Cornelius et al. |
| 5,951,494 | A | 9/1999 | Wang et al. |
| 6,001,068 | A | 12/1999 | Uchino et al. |
| RE36,628 | E | 3/2000 | Sagae et al. |
| 6,093,157 | A | 7/2000 | Chandrasekaran |
| 6,165,292 | A | 12/2000 | Abrams et al. |
| 6,234,981 | B1 | 5/2001 | Howland |
| 6,390,992 | B1 | 5/2002 | Morris et al. |
| 6,520,923 | B1 | 2/2003 | Jalisi |
| 6,679,853 | B1 | 1/2004 | Jalisi |
| 7,182,735 | B2 | 2/2007 | Shireman et al. |
| 2004/0030266 | A1 | 2/2004 | Murayama et al. |
| 2004/0039308 | A1 | 2/2004 | Murayama et al. |
| 2004/0039309 | A1 | 2/2004 | Murayama et al. |
| 2005/0065456 | A1 | 3/2005 | Eskuri |
| 2005/0152731 | A1 | 7/2005 | Mishima et al. |
| 2006/0041204 | A1 | 2/2006 | Kato |

FOREIGN PATENT DOCUMENTS

| | | |
|---|---|---|
| JP | 10-146390 A | 6/1998 |
| WO | WO 2006/055201 A1 | 5/2006 |

OTHER PUBLICATIONS

European Search Report.

* cited by examiner

GUIDE WIRE

This application claims priority under 35 U.S.C. §119(e) with respect to U.S. provisional Application No. 60/878,663 filed on Dec. 28, 2006, and is also based on and claims priority under 35 U.S.C. §119(a) with respect to Japanese Application No. 2006-356642 filed on Dec. 28, 2006 and Japanese Application No. 2007-169347 filed on Jun. 27, 2007, the entire content of all three of which is incorporated herein by reference.

TECHNOLOGICAL FIELD

The subject matter disclosed here generally pertains to a medical implement. More specifically, the subject matter relates to a guide wire.

BACKGROUND DISCUSSION

Guide wires are used to guide catheters for use in the treatment of body regions that are difficult to operate on surgically, the treatment of body regions through minimally invasive surgery, and the inspection of blood vessels by cardiac angiography. For example, to perform PCI (Percutaneous Coronary Intervention) under X-ray radioscopy, the distal end of a guide wire is placed to project from the distal end of a balloon catheter, and the guide wire together with the balloon catheter is inserted into the blood vessel up to a position near the constricted area of the coronary artery in question for guiding the distal end of the balloon catheter to the position near the constricted area.

An example of a guide wire used in the above treatment is disclosed in U.S. Pat. No. 5,797,857. The disclosed guide wire includes a flexible wire body (core), a coil (a metal coil for X-ray angiography) disposed in surrounding relation to the distal end of the wire body, and a covering layer (a covering member of synthetic resin, a hydrophilic lubricating layer) covering the outermost surfaces of the wire body and the coil.

When the guide wire disclosed in U.S. Pat. No. 5,797,857 is used to guide the catheter as described above, the following phenomena tend to occur depending on the state of the coronary artery such as the degree of curvature of the coronary artery:

If the guide wire is pushed in when the coil of the guide wire reaches (is inserted into) a sharp bend of the coronary artery, for example, undue forces (tending to cause a plastic deformation) are liable to be applied to the coil. At this time, a turn of the wire of the coil rides onto an adjacent turn of the wire, thus tending to plastically deform the coil. Therefore, the coil will not recover its ordinary (normal) state, and the pushing force applied from the proximal end of the wire body will not be reliably transmitted to the distal end of the wire body, i.e., the guide wire pushing capability is greatly reduced.

Though the coil of the guide wire disclosed in U.S. Pat. No. 5,797,857 has the hydrophilic lubricating layer, a relatively large frictional resistance is developed between the hydrophilic lubricating layer and a sharp bend of the coronary artery depending on the thickness of the guide wire when the coil of the guide wire reaches (is inserted into) the sharp bend of the coronary artery. Therefore, the torque from the proximal end of the guide wire is not reliably transmitted through the coil to the distal end of the wire body, i.e., the torque transmitting capability is greatly reduced.

SUMMARY

One of the present invention includes a guide wire including a wire body having a tapered portion disposed on a distal end portion thereof and having an outside diameter progressively reduced toward a distal end thereof. The guide wire includes a coil disposed in covering relation to the distal end portion of the wire body and including a helically shaped wire. The coil includes an increasing wire-diameter portion where the diameter of the wire increases continuously toward a distal end thereof. The increasing wire-diameter portion is disposed in covering relation to the outer circumference of at least a portion of the tapered portion in a longitudinal direction.

The wire body and the coil can be configured so that they are spaced from each other by a clearance distance which is substantially constant along a longitudinal direction of the wire body.

According to another aspect, a guide wire includes a wire body having a tapered portion disposed on a distal end portion thereof and having an outside diameter progressively reduced toward a distal end thereof. The guide wire includes a coil disposed in covering relation to the distal end portion of the wire body and including a helically shaped wire. The coil includes an increasing wire-diameter portion where the diameter of the wire increases stepwise toward a distal end thereof, with the increasing wire-diameter portion being disposed in covering relation to the outer circumference of at least a portion of the tapered portion in a longitudinal direction.

The wire body and the coil are preferably spaced from each other by a clearance distance which is maximum at a most distal end of the increasing wire-diameter portion. The coil preferably has an outside diameter which is substantially constant along a longitudinal direction thereof. The coil is preferably disposed adjacent to a proximal end of the increasing wire-diameter portion, and includes a constant wire-diameter portion where the diameter of the wire is substantially constant. The diameter of the constant wire-diameter portion is preferably equal to or less than the minimum diameter of the increasing wire-diameter portion.

The increasing wire-diameter portion and the constant wire-diameter portion can include a single wire. Alternatively, the increasing wire-diameter portion and the constant wire-diameter portion can include two individual wires. The boundary between the increasing wire-diameter portion and the constant wire-diameter portion preferably includes a biting portion where the wires mesh with each other. In addition, a plurality of fixing materials by which the coil is fixed to the wire body at a plurality of locations can be provided, with the fixing materials being disposed at positions other than the biting portion.

The increasing wire-diameter portion and the constant wire-diameter portion can be made of the same material or different materials. Adjacent turns of the wire of the increasing wire-diameter portion can be spaced from each other or can contact each other in the absence of an externally applied force to the guide wire.

According to a further aspect, a guide wire includes a wire body having a tapered portion disposed on a distal end portion thereof and having an outside diameter progressively reduced toward a distal end thereof. The guide wire includes a first coil disposed in covering relation to the distal end portion of the wire body and including a helically shaped first wire. In addition, a second coil is positioned within the first coil and includes a helically shaped second wire disposed in covering relation to the outer circumference of at least a portion of the tapered portion in a longitudinal direction.

The guide wire may further include a first clearance defined between the first coil and the second coil, and a second clearance defined between the second coil and the wire body. The first clearance preferably has a clearance distance which is constant along a longitudinal direction of the wire body. The second clearance preferably has a clearance distance which is progressively greater toward the distal end. Adjacent turns of the first wire of the first coil can be in contact with each other or spaced from each other in a portion corresponding in longitudinal extent to the tapered portion, and adjacent turns of the second wire of the second coil can be spaced apart from each other. The guide wire further may include at least one fixing material by which the second coil is preferably fixed to the wire body, wherein the fixing material is disposed on a distal end portion of the second coil. The fixing material should preferably be disposed in a portion other than the proximal end portion of the second coil.

The fixing material should also preferably be used to fix the first coil to the wire body. The average diameter of the second wire should preferably be greater than the average diameter of the first wire.

BRIEF DESCRIPTION OF THE DRAWING FIGURES

The above and other aspects and features will become apparent from the following detailed description considered with reference to the accompanying drawing figures which illustrate embodiments of the disclosed device by way of example.

DETAILED DESCRIPTION

Figure 1:
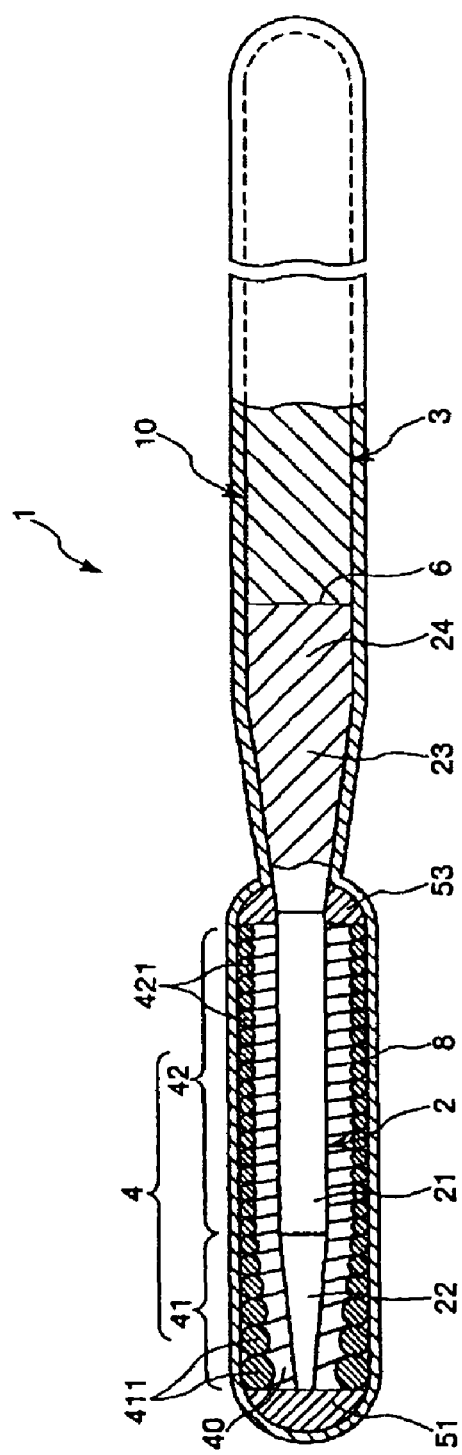
FIG. 1 is a partly longitudinal cross-sectional view of a guide wire according to one embodiment.
Figure 2:
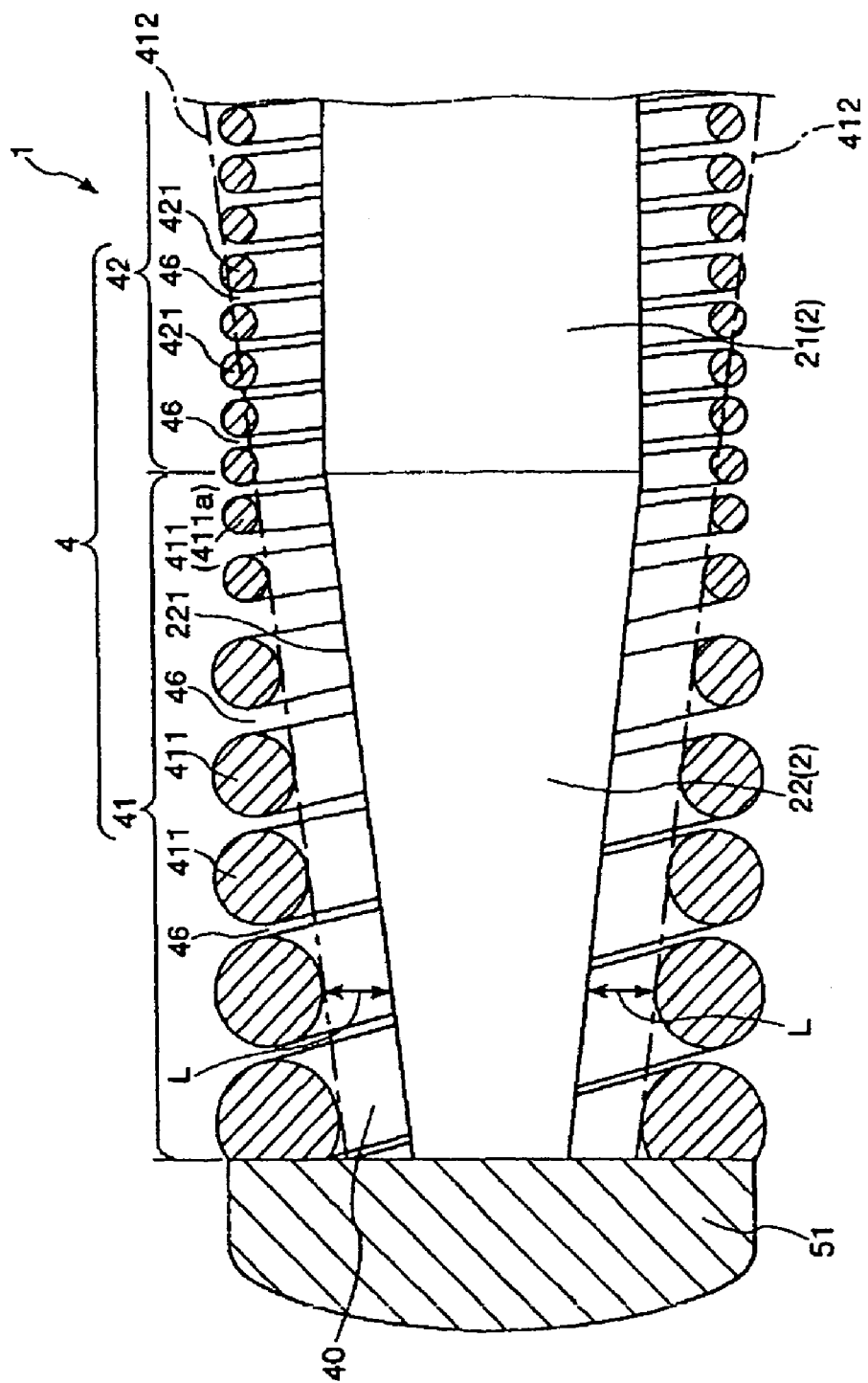
FIG. 2 is an enlarged detailed cross-sectional view of a tapered portion of the guide wire shown in FIG. 1.

A first embodiment of the guide wire is illustrated in FIGS. 1 and 2. In the description that follows, the rightward end in FIGS. 1 and 2 (also FIGS. 3-10) are referred to as the "proxi-mal end" and the leftward end is referred to as the "distal end." For ease in understanding, the guide wire is shown in FIGS. 1 and 2 (and FIGS. 3-10) at a reduced scale in its longitudinal direction, and at an exaggerated scale in its transverse direction. It is thus to be understood that the illustrated ratio between the longitudinal and transverse dimensions is different from the actual ratio. Also, in FIG. 2, as well as FIGS. 3 and 5-10, the resin coating layer (described below) is omitted from illustration.

The guide wire 1 shown in FIG. 1 is a catheter guide wire configured to be inserted into the lumen of a catheter (including an endoscope). The guide wire 1 includes a wire body 10 and a helical coil 4 disposed on the distal end portion (a portion near the distal end) of the wire body 10. The wire body 10 includes a distally disposed first wire 2 and a proximally disposed second wire 3, with the distal end of the second wire 3 being joined (coupled) to the proximal end of the first wire 2, preferably by welding. The total length of the guide wire 1 is not limited to any value, but should preferably be in the range from about 200 to 5000 mm.

The first wire 2 is made of a wire material which is flexible or elastic. The length of the first wire 2 is not limited to any value, but should preferably be in the range from about 20 to 1000 mm.

The first wire 2 includes a constant-diameter portion 21 having a constant (inclusive of substantially constant) outside diameter, a tapered portion 22 positioned on a distal end of the constant-diameter portion 21 and having an outside diameter progressively decreasing toward the distal end, a tapered portion 23 positioned on a proximal end of the constant-diameter portion 21 and having an outside diameter progressively greater toward the proximal end, and a constant-diameter portion 24 positioned on a proximal end of the tapered portion 23 and having a constant (inclusive of substantially constant) outside diameter. Since the first wire 2 possess the noted shape, i.e., a tapered shape, the rigidity (bending rigidity, torsional rigidity) of the first wire 2 is progressively reduced toward the distal end. As a result, the distal end portion of the guide wire 1 is capable of passing through constricted portions and is flexible, so that the guide wire 1 has an increased ability to follow blood vessels or the like, is highly safe, and is inhibited from being kinked.

The taper angle (the rate at which the outside diameter decreases) of the tapered portions 22, 23 may be constant along the longitudinal direction of the wire or may vary along the longitudinal direction of the wire. For example, the tapered portions may have a plurality of alternately repetitive regions where the taper angle (the rate at which the outside diameter decreases) is relatively large and relatively small.

The constant-diameter portion 21 is constant in outside diameter along the longitudinal direction of the wire (from the proximal end of the tapered portion 22 to the distal end of the tapered portion 23). The length of the constant-diameter portion 21 should preferably be greater than the length of a constant-wire-diameter portion (second coil) 42 described in more detail below.

The constant-diameter portion 24 has its outside diameter constant along the longitudinal direction of the wire (up to the proximal end of the first wire 2). The second wire 3 has its distal end joined (coupled) to the proximal end of the first wire 2 (the proximal end of the constant-diameter portion 24), preferably by welding. The second wire 3 is made of a wire material which is flexible or elastic.

The welding process by which the first wire 2 and the second wire 3 may be welded to each other is not limited to any particular welding processes. For example, the welding process may be friction welding, laser-beam spot welding, butt resistance welding such as upset welding, or the like. Butt resistance welding is preferable as it can achieve relatively high bonding strength relatively easily.

In the present embodiment, the second wire 3 is substantially constant in outside diameter along the longitudinal direction of the wire. The outside diameter of the second wire 3 is substantially the same as the outside diameter of the constant-diameter portion 24 of the first wire 2. Therefore, when the proximal end of the constant-diameter portion 24 of the first wire 2 and the distal end of the second wire 3 are joined to each other, no step is produced on the outer circumferential surface of their joint (welded region) 6 due to any outside diameter difference between the wires 2, 3. Thus, a continuous and smooth surface exists between the two wires 2, 3.

The average outside diameter of the first wire 2 is smaller than the average outside diameter of the second wire 3. Average outside diameter refers to the outside diameter obtained by measuring the outside diameter of the wire at five randomly chosen places and spaced apart locations (in different diameter sections, if appropriate), and averaging the diameter obtained at the five locations. Preferably, for the first wire 2, the outside diameter would be measured at five spaced apart locations so that at least one measurement is taken in each of the sections 21, 22, 23, 24. With the average outside diameter of the first wire 2 being smaller than the average outside diameter of the second wire 3, the guide wire 1 is flexible at the first wire 2 on the distal end portion thereof, and is relatively highly rigid at the second wire 3 on the proximal end portion thereof. Consequently, the guide wire 1 has both flexibility at the distal end portion and excellent operability (pushing capability, the torque transmitting capability, etc.).

The material of the first wire 2 and the second wire 3 is not limited to any materials. For example, each of the first wire 2 and the second wire 3 may be made of any of various metal materials including stainless steel (e.g., all types such as type 304, 303, 316, 316L, 316J1, 316J1L, 405, 430, 434, 444, 429, 430F, 302), piano wire, cobalt-based alloy, pseudoelastic alloy (including superelastic alloy), etc. Of these metal materials, pseudoelastic alloy (including superelastic alloy) is particularly preferable, and superelastic alloy is more preferable.

The superelastic alloy is relatively pliable, has recoverability, and is less liable to remain bent when it is bent. If the first wire 2 is made of superelastic alloy, the distal end portion of the guide wire 1 is sufficiently flexible and recoverable when it is bent, has an increased ability to follow blood vessels that are curved and bent intricately, and is of excellent operability. Furthermore, as the first wire 2 is less liable to remain bent due to its recoverability even when the first wire 2 is repeatedly curved and flexurally deformed, the first wire 2 is prevented from having its operability lowered due to the tendency to remain bent which would otherwise be developed during use of the guide wire 1.

The superelastic alloy includes those which exhibit different tensile stress vs. strain curves (i.e., the superelastic alloys which can be used here are not limited to superelastic alloys having a particular tensile stress vs. strain curve), those which have transformation points such As (austenite start temperature), Af (austenite finish temperature), Ms (martensite start temperature), Mf (martensite finish temperature), etc. measurable clearly or not, and those which are largely deformed (strained) under stresses and return to their original shape upon removal of the stresses.

Preferable compositions of the superelastic alloy include Ni—Ti-based alloy such as Ni—Ti alloy containing 49 to 52 atomic % of Ni, Cu—Zn alloy containing 38.5 to 41.5 weight % of Zn, Cu—Zn—X alloy (X represents at least one of Be, Si, Sn, Al, and Ga) containing 1 to 10 weight % of X, Ni—Al alloy containing 36 to 38 atomic % of Al, etc. Of these alloys, the Ni—Ti-based alloy is particularly preferable. The superelastic alloy, which is typified by the Ni—Ti-based alloy, is also excellent in its ability to adhere closely to a resin covering layer 8 to be described later.

The cobalt-based alloy in the form of a wire has a high modulus of elasticity and has an appropriate elastic limitation. Therefore, a wire made of cobalt-based alloy has excellent torque transmitting capability and is highly less susceptible to problems such as buckling. Any cobalt-based alloys may be used insofar as they contain Co as a component. However, cobalt-based alloys which contain Co as a chief component (cobalt-based alloys: alloys containing Co at a highest weight ratio among the elements of the alloy) are preferable, and Co—Ni—Cr-based alloy is more preferable. The alloys of these compositions make the above advantages better. The wire of the alloys of these compositions have a high modulus of elasticity, can be cold-formed even if they have a high elastic limit, and can be reduced in diameter while sufficiently preventing themselves from buckling because of the high elastic limit. The wire of these alloys is flexible and rigid enough to be inserted into a given region.

The first wire 2 and the second wire 3 may be made of different materials, or may be made of the same metal material or metal materials of the same kind (containing the same main metal in alloys). The first wire 2 and the second wire 3 thus constructed provide a higher bonding strength at the junction (welded region) 6, are generally not susceptible to being torn apart even if the outside diameter of the joint 6 is small, and exhibit excellent torque transmitting capability.

If the first wire 2 and the second wire 3 are made of different materials, the first wire 2 should preferably be made of superelastic alloy referred to above, and more preferably be made of Ni—Ti-based alloy, and the second wire 3 should preferably be made of stainless steel.

The coil 4 is disposed around the distal end portion of the wire body 10 in covering relation thereto. The coil 4 thus placed on the distal end portion of the wire body 10 reduces the area of contact of the wire body 10 with the inner wall of the catheter and the living body surface, resulting in reduced sliding resistance. As a result, the operability of the guide wire 1 is increased.

The coil 4 includes a single wire having a circular cross-sectional area and helically shaped. The wire forming the coil 4 includes a section where the outside diameter varies (progressively decreases) along the longitudinal direction and a section having a constant outside diameter. The section having the constant outside diameter is disposed contiguously from (immediately adjacent to) the end of the first-mentioned section having a minimum outside diameter. The coil 4 is formed by helically winding the wire.

As shown in FIGS. 1 and 2, the coil 4 is comprised of two portions, an increasing wire-diameter portion (first coil) 41 where the wire diameter of a wire 411 continuously increases toward the distal end and a constant wire-diameter portion (second coil) 42 where the wire diameter of a wire 421 is constant (inclusive of substantially constant).

Since the coil 4 includes a single wire, the mechanical strength of the coil is inhibited from largely changing (decreasing) at the boundary between the increasing wire-diameter portion 41 and the constant wire-diameter portion 42. Therefore, the coil 4 is reliably inhibited from being undesirably deformed (e.g., bent over at the boundary between the increasing wire-diameter portion 41 and the constant wire-diameter portion 42) when the guide wire 1 is operated.

As shown in FIGS. 1 and 2, the increasing wire-diameter portion 41 is disposed on the distal end portion of the coil 4 and the constant wire-diameter portion 42 on the proximal end portion of the coil 4. The coil 4 is spaced from the wire body 10 so that a clearance 40 is defined between the inner surface of the coil and the outer surface of the wire body 10. The coil 4 is thus held out of contact with the wire body 10. The increasing wire-diameter portion 41 covers the outer circumference of the entire tapered portion 22 of the first wire 2, and the constant wire-diameter portion 42 covers the outer circumference of the constant-diameter portion 21 of the first wire 2.

The increasing wire-diameter portion 41 has its inside diameter progressively decreasing toward the distal end. The outside diameter of the tapered portion 22 is also progressively smaller toward the distal end in a manner corresponding to (i.e., so as to follow) the decreasing inside diameter of the increasing wire-diameter portion 41, thereby minimizing the size of the clearance 40. The decreasing inner diameter of the increasing wire-diameter portion 41 preferably decreases at a rate equal to the rate of decrease of the outside diameter of the tapered portion 22. Accordingly, when the guide wire 1 is operated in a living body, i.e., when the guide wire 1 is pushed in from the proximal end thereof, helical turns of the wire 411 (also the wire 421) are reliably inhibited from riding onto an adjacent turn. The guide wire 1 can thus be used in a normal state, i.e., the pushing forces can reliably be transmitted to the distal end of the guide wire 1.

The outside diameter of the tapered portion 22 is reduced toward the distal end. Since the wire diameter of the increasing wire-diameter portion 41 which covers the tapered portion 22 increases toward the distal end, the mechanical strength of the distal end portion of the guide wire 1 is not greatly reduced.

The disclosed guide wire 1 thus possesses excellent operational characteristics during use.

As shown in FIG. 2, the distance L of the clearance 40 (clearance distance) is constant along the longitudinal direction of the wire. The "distance L" refers to the distance between a tangential line 412 that is tangential to the inner circumferential surface of the coil 4 of the increasing wire-diameter portion 41 and the outer circumferential surface 221 of the tapered portion 22.

Since the distance L is constant, the advantages provided by the minimum size of the clearance 40 of the guide wire 1 are made better. At the same time, a certain space (clearance) is provided between the inner surface of the increasing wire-diameter portion 41 and the outer surface of the first wire 2 (the tapered portion 22), making the portion of the guide wire 1 at the increasing wire-diameter portion 41 more pliable.

The outside diameter of the coil 4 is constant along the longitudinal direction of the wire. Therefore, the resistance to the insertion of the guide wire 1 into a catheter or a living body is reduced. Moreover, the turns of the wire 411 are reliably inhibited from riding onto an adjacent turn when the guide wire 1 is pushed in.

According to the present embodiment, the diameter of the wire 421 of the constant-wire-diameter portion 42 is the same as the minimum diameter of the wire 411 of the increasing wire-diameter portion 41, i.e., the diameter of the wire 411a positioned on the most proximal end of the increasing wire-diameter portion 41 in FIG. 2. Therefore, the mechanical strength is restrained from being greatly reduced at the boundary between the constant-wire-diameter portion 42 and the increasing wire-diameter portion 41. Therefore, the coil 4 is reliably inhibited from being undesirably deformed, e.g., bent over at the boundary between the increasing wire-diameter portion 41 and the constant wire-diameter portion 42, when the guide wire 1 is operated. The coil 4 is also prevented from damaging, or being stuck on, an associated device due to a coil shift in a tortuous region of the blood vessel.

The diameter of the wire 421 is not limited to being the same as the diameter of the wire 411a, and may be slightly smaller than the diameter of the wire 411a.

As shown in FIG. 2, adjacent turns of the wires 411, 421 are spaced from each other in the absence of external forces in the increasing wire-diameter portion 41 and the constant wire-diameter portion 42. Therefore, gaps 46 are provided between the adjacent turns of the wire 411 (and also the wire 421). When the guide wire 1 is inserted into a catheter or a living body, forces that the guide wire 1 receives from its distal end are reduced or taken-up by the gaps 46, so that adjacent turns of the wire 411 are less susceptible to riding onto each other. Therefore, the gaps 46 function as a damping means for reducing the forces that the guide wire 1 receives from its distal end.

The coil 4 (the wires 411, 421) may be made of either a metal material or a resin material.

The metal material of the coil 4 may be the same as the materials referred to above in the description of the first wire 2 and the second wire 3. Other metals for use as the material of the coil 4 may include a cobalt-based alloy, a precious metal such as gold, platinum, tungsten, or the like, or an alloy containing any of these materials (e.g., a platinum-iridium alloy). If the coil 4 is made of an X-ray-impermeable material such as a precious metal, then the guide wire 1 becomes compatible with X-ray angiography, so that the guide wire 1 can be inserted into a living body while the distal end portion thereof is being positionally confirmed under X-ray angiography.

The wires of the coil 4 are circular in cross-sectional shape. However, the wires are not limited to this circular cross-sectional shape, but may be of an elliptical cross-sectional shape, a quadrangular (particularly, rectangular) cross-sectional shape, or the like.

As shown in FIG. 1, the coil 4 is fixed to the wire body 10 at two locations. Specifically, the distal end of the increasing wire-diameter portion 41 is fixed to the distal end of the first wire 2 (the tapered portion 22) by a fixing material (fixing member) 51. The proximal end of the constant wire-diameter portion 42 is fixed to an intermediate portion of the first wire 2 (near the boundary between the constant-outside-diameter portion 21 and the tapered portion 23) by a fixing material (fixing member) 53. By thus fixing the coil 4 at the above locations, the increasing wire-diameter portion 41 and the constant wire-diameter portion 42 are reliably fixed in position without impairing the flexibility of the distal end portion of the guide wire 1 (where the coil 4 is present).

The fixing materials 51, 53 are preferably made of solder (brazing material). The fixing materials 51, 53 are not limited to solder, but may be an adhesive. The means by which the coil 4 is fixed to the wire body 10 is not limited to fixing materials, but may be provided by welding, for example. In order to prevent damage to the inner wall of a lumen such as a blood vessel or the like, the distal end surface of the fixing material 51 should preferably be rounded.

As shown in FIG. 1, the entire (or partial) outer surface of the guide wire 1 is covered with a resin covering layer 8. The resin covering layer 8 may be formed for various purposes. For example, the resin covering layer 8 serves to reduce the friction (frictional resistance) of the guide wire 1 for increased slidability to increase the operability of the guide wire 1.

In order to reduce the friction (frictional resistance) of the guide wire 1, the resin covering layer 8 should preferably be made of a material capable of reducing friction as described below. The frictional resistance (sliding resistance) between the guide wire 1 and the inner wall of the catheter that is used with the guide wire 1 is reduced to increase slidability, allowing the guide wire 1 to be well operated in the catheter. Moreover, since the sliding resistance to the guide wire 1 is reduced, when the guide wire 1 is moved and/or turned in the catheter, the guide wire 1 is reliably prevented from being kinked or twisted particularly in the vicinity of the joint 6.

Examples of the material forming the covering layer 8 and capable of reducing friction include may be polyolefin such as polyethylene, polypropylene, or the like, polyvinyl chloride, polyester (PET, PBT, or the like), polyamide, polyimide, polyurethane, polystyrene, polycarbonate, silicone resin, fluororesin (PTFE, ETFE, or the like), or a composite material thereof.

The resin covering layer 8 may also be provided for the purpose of increasing safety upon insertion of the guide wire 1 into a blood vessel or the like. To serve this purpose, the resin covering layer 8 should preferably be made of a relatively highly pliable material (soft material, elastic material).

Examples of relatively highly pliable material include polyolefin such as polyethylene, polypropylene, or the like, polyvinyl chloride, polyester (PET, PBT, or the like), polyamide, polyimide, polyurethane, polystyrene, silicone resin, thermoplastic elastomer such as polyurethane elastomer, polyester elastomer, polyamide elastomer, or the like, any of various rubber materials such as latex rubber, silicone rubber, or the like, or a composite material including two or more of the above materials in combination.

The resin covering layer 8 may be a single layer or a laminated body of two or more layers.

At least the outer surface of the distal end portion of the guide wire 1 should preferably be coated with a hydrophilic material. The hydrophilic material is wetted to provide lubrication for thereby reducing friction (sliding resistance) of the guide wire 1 for increased slidability. Therefore, the operability of the guide wire 1 is increased.

The hydrophilic material may be cellulose-based polymeric material, polyethylene-oxide-based polymeric material, maleic-anhydride-based polymeric material (e.g., maleic anhydride copolymer such as methylvinylether-maleic anhydride copolymer), acrylamide-based polymeric material (e.g., polyacrylamide or polyglycidylmethacrylate-dimethylacrylamide (PGMA-DMMA) block copolymer), water-soluble nylon, polyvinyl alcohol, polyvinyl pyrrolidone, or the like.

When the hydrophilic material is wetted (absorbs water), it provides lubrication to reduce friction (sliding resistance) between the guide wire 1 and the inner wall of the catheter that is used with the guide wire 1. The slidability of the guide wire 1 is increased to improve the operability of the guide wire 1 in the catheter.

Figure 3:
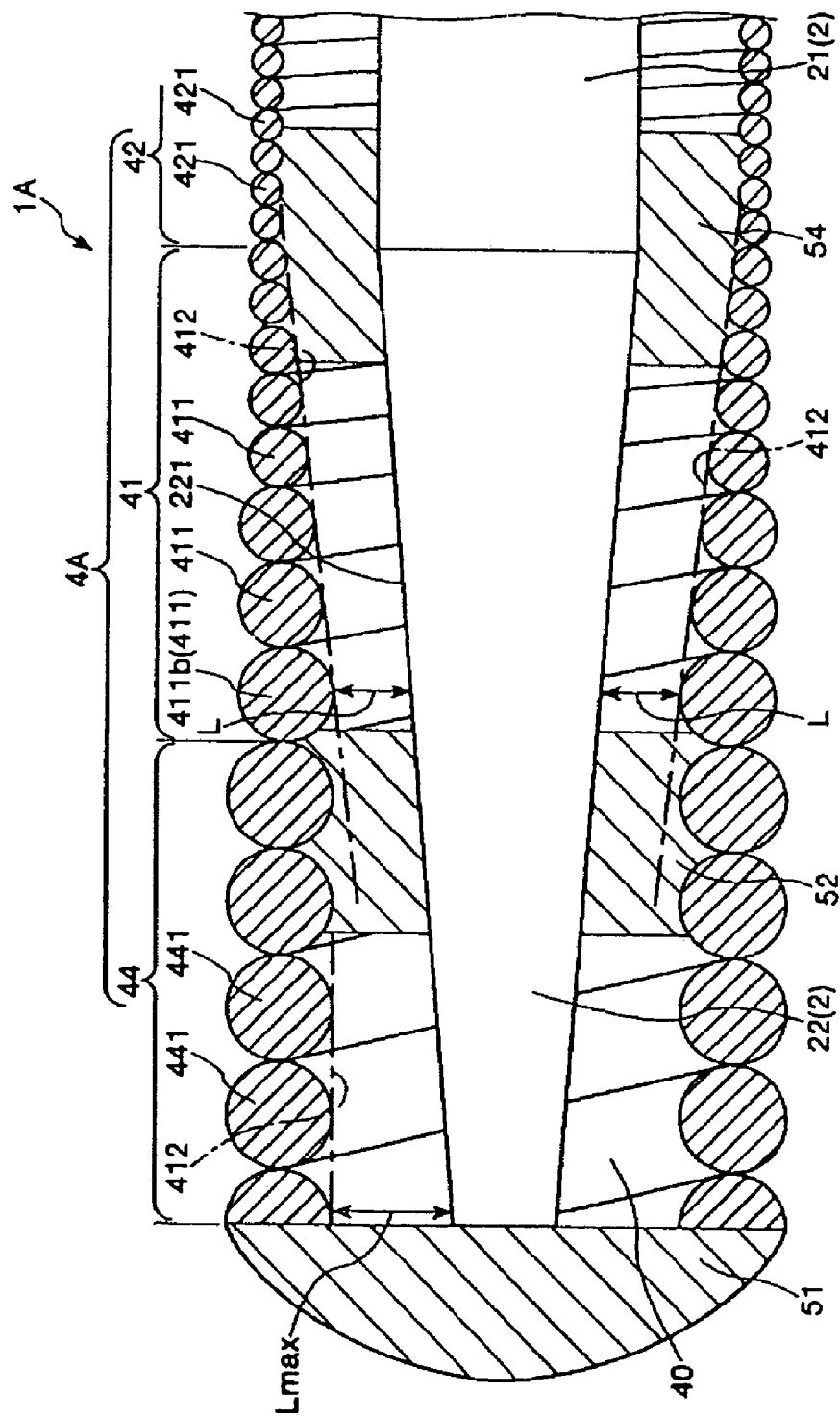
FIG. 3 is an enlarged detailed cross-sectional view showing a tapered portion of a guide wire according to another embodiment.

FIG. 3 illustrates a tapered portion of a guide wire according to a second embodiment. The description below of the guide wire according to this second embodiment will primarily address aspects of the guide wire different from those associated with the first embodiment. Features of the second embodiment similar to those in the first embodiment are identified by the same reference numeral and a detailed description of such features is not repeated.

The second embodiment of the guide wire differs from the first embodiment primarily with respect to the structure of the coil. The coil 4A of the guide wire 1A shown in FIG. 3 also has, in addition to the increasing wire-diameter portion 41 and the constant wire-diameter portion 42, a constant wire-diameter portion 44 disposed on the distal end of the increasing wire-diameter portion 41.

The constant wire-diameter portion 44 is unitarily formed in one piece (integrally with) contiguously to the increasing wire-diameter portion 41. The constant wire-diameter portion 44 includes a wire 441 whose diameter is identical to or slightly greater than the maximum diameter of the wire 411 of the increasing wire-diameter portion 41, i.e., the diameter of the wire 411b positioned at the most distal end shown in FIG. 3. In this illustrated embodiment, the constant wire-diameter portion 44 and the increasing wire-diameter portion 41 cover the tapered portion 22 in its entirety.

As shown in FIG. 3, the distance L of the clearance 40 is maximum (maximum distance $L_{max}$) at the constant wire-diameter portion 44 (the distal end portion of the coil 4A), and the distance L is smaller than the maximum distance $L_{max}$ in the portion of the coil 4A except for the constant wire-diameter portion 44. The size of the clearance 40 is thus minimized, making the advantages thereof better, i.e., making it more effective to prevent adjacent turns of the wire 411 (also the wires 441, 421) from riding on one another when the guide wire 1A is pushed in.

As shown in FIG. 3, the distance L representing the clearance (clearance distance) in the increasing wire-diameter portion 41 is constant along the longitudinal direction of the wire. The "distance L" refers to the distance between a line (tangential line) 412 tangential to the inner circumferential surface of the coil 4 of the increasing wire-diameter portion 41 and the outer circumferential surface 221 of the tapered portion 22. The diameter of the wire 411 should preferably vary and should preferably be equal to or greater than L/3. By virtue of the distance L of the clearance 40 being constant and the diameter of the wire 411 being equal to or greater than L/3, the minimized clearance 40 more effectively helps prevent adjacent turns or windings of the wire 411 from riding on one another when the guide wire 1A is pushed in.

The coil 4A is fixed to the wire body 10 at four locations. As with the coil 4 according to the first embodiment, two of the four locations are the distal end of the coil 4A (the constant wire-diameter portion 44) and the proximal end of the coil 4A (the constant wire-diameter portion 42). The remaining two locations are the proximal end of the constant wire-diameter portion 44 (which may partly overlap the distal end of the increasing wire-diameter portion 41) and the boundary between the increasing wire-diameter portion 41 and the constant wire-diameter portion 42. The proximal end of the constant wire-diameter portion 44 is fixed to an intermediate portion of the tapered portion 22 of the first wire 2 by a fixing material 52, and the boundary between the increasing wire-diameter portion 41 and the constant wire-diameter portion 42 is fixed to the boundary between the tapered portion 22 and the constant-diameter portion 21 by a fixing material 54.

By thus fixing the coil 4A at the above locations (four locations), the coil 4A can be reliably fixed in position without significantly impairing the flexibility of the distal end portion of the guide wire 1 (where the coil 4 is present).

In each of the constant wire-diameter portion 44, the increasing wire-diameter portion 41, and the constant wire-diameter portion 42, adjacent turns of the wires (the wires 441, 411, 421) are held in close contact with each other, i.e., are closely arranged with no gaps therebetween, when no external forces are applied to the coil 4A. Thus, when the guide wire 1 is inserted into a catheter or a living body, friction occurs between the adjacent turns of the wire 411 (also the wire 441, 421). As a result, the adjacent turns of the wire 411 are generally not susceptible to being positionally displaced, i.e., two adjacent turns of the wire 411 are reliably inhibited from riding on one another other.

The constant wire-diameter portion 44 (the wire 441), the increasing wire-diameter portion 41 (the wire 411), and the constant wire-diameter portion 42 (the wire 421) of the coil 4A may be made of the same material, or may be made of different materials. According to a preferable example, the wire 441 may be made of an X-ray-impermeable material (e.g., a Pt—Ni alloy), and the wires 411, 421 may be made of a material which is relatively permeable to an X-ray (e.g., stainless steel).

The coil 4A which has different portions made of different materials may be manufactured by various processes which are not limited to a specific method. For example, the coil 4A may be manufactured by the method to be described below.

First, a first member 201 in the form of a rod (cylinder) made of stainless steel and a second member 402 in the form of a rod (cylinder) made of a Pt—Ni alloy are prepared. These members have the same outside diameter.

Figure 4A:
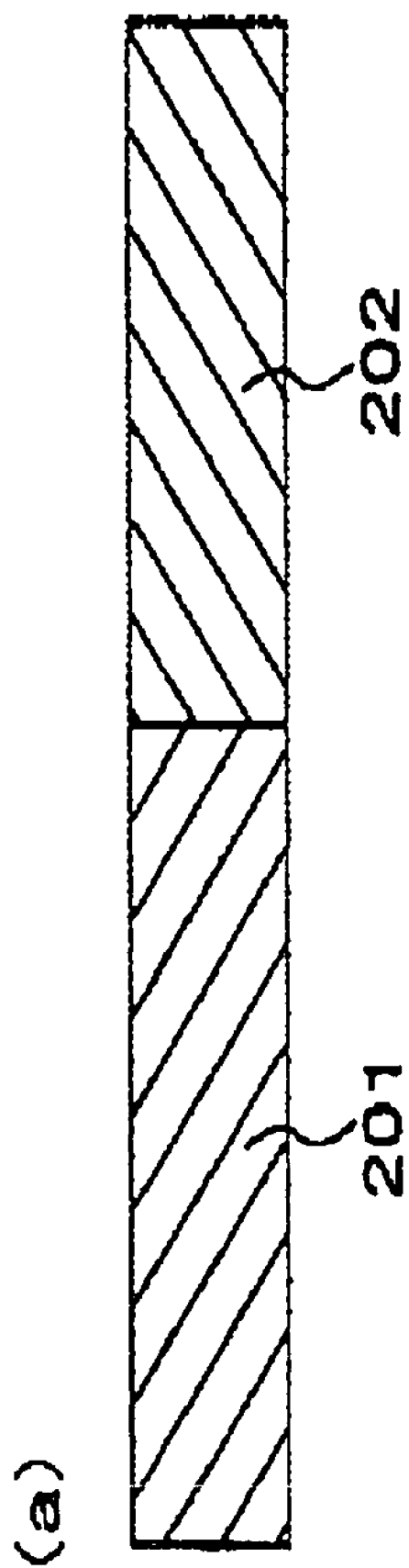
FIGS. 4A-4C are cross-sectional views schematically showing aspects of a method of manufacturing a coil of the guide wire shown in FIG. 3.

Then, as shown in FIG. 4A, respective end faces of the first member 201 and the second member 202 are joined to each other by laser beam spot welding, for example.

Figure 4B:
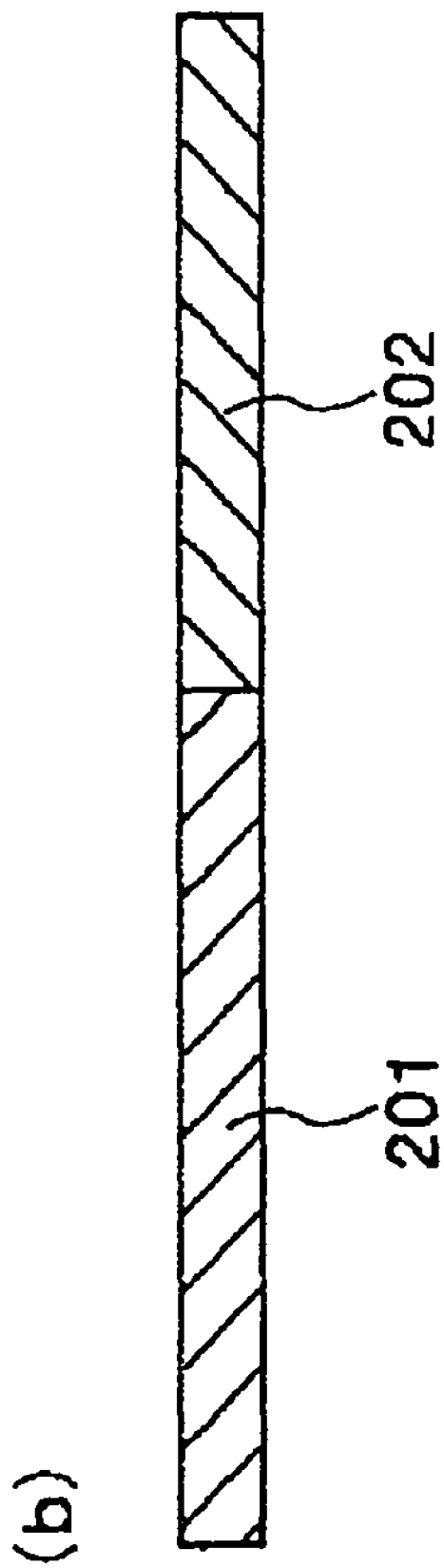

Then, the first member 201 and the second member 202 that are joined to each other are threaded or passed through a die, for example. As shown in FIG. 4B, the first member 201 and the second member 202 are reduced (squeezed) to a predetermined outside diameter.

Figure 4C:
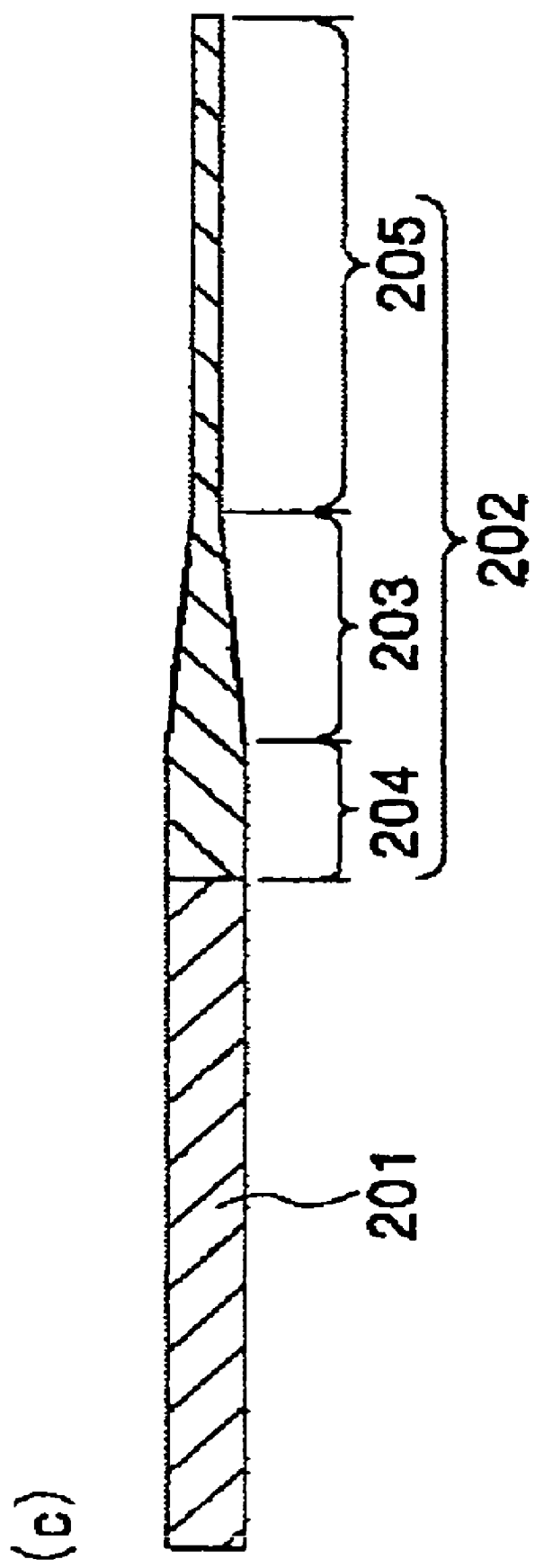

Of the first member 201 and the second member 202 which are produced as shown in FIG. 4B, a portion of the second member 202 is passed or threaded through a die or polished or ground until it is squeezed to a predetermined outside diameter, thereby producing a wire shown in FIG. 4C (the outside diameter of a portion of the second member 202 is progressively reduced toward the proximal end). The portion of the second member 202 whose outside diameter is the same as the outside diameter of the first member 201 and is constant is referred to as "the portion 204", the portion of the second member 202 whose outside diameter is progressively reduced toward the proximal end is referred to as "the portion 203", and the portion of the second member 202 which is positioned on the proximal end of the portion 203 and whose outside diameter is constant is referred to as "the portion 205". The wire shown in FIG. 4C is then helically wound into the coil 4A.

With the coil 4A thus produced, the helical first member 201 forms the constant-wire-diameter portion 44, the helical portion 203 (including the portion 204) forms the increasing wire-diameter portion 41, and the helical portion 205 forms the constant-wire-diameter portion 42.

Figure 5:
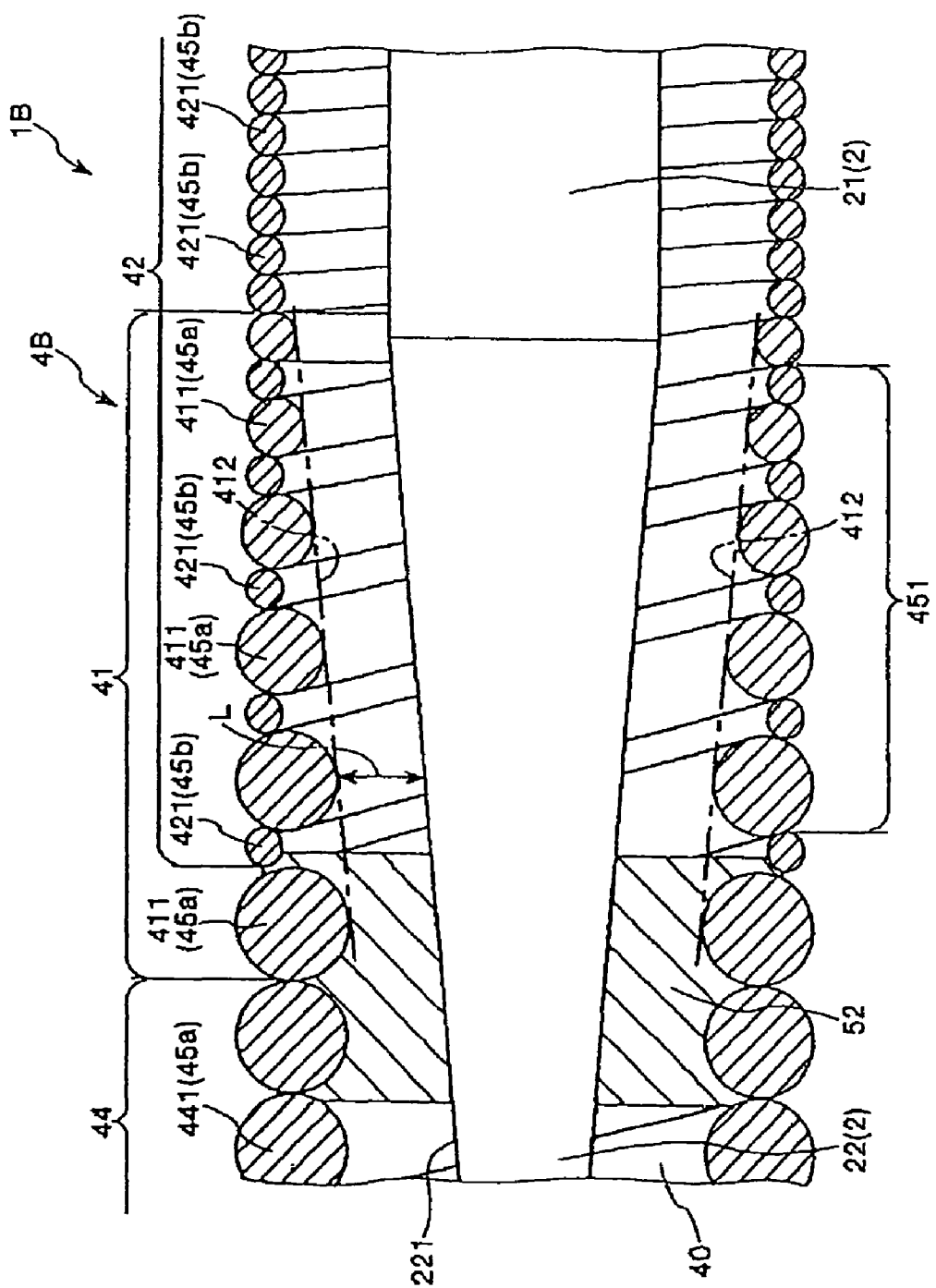
FIG. 5 is an enlarged detailed cross-sectional view showing a tapered portion of a guide wire according to a third embodiment of the present invention.

FIG. 5 illustrates a tapered portion of a guide wire according to a third embodiment. The description below of the guide wire according to this third embodiment will primarily address aspects of the guide wire different from those associated with the previously described embodiments. Features of the third embodiment similar to those in the previously described embodiments are identified by the same reference numeral and a detailed description of such features is not repeated.

The third embodiment shown in FIG. 5 is similar to the second embodiment except for the structure of the coil. The coil 4B of the guide wire 1B shown in FIG. 5 includes two wires 45a, 45b each helically wound.

The wire 45a has a portion (wire 441) having an outside diameter (wire diameter) which is constant and a portion (wire 411) having an outside diameter (wire diameter) which is progressively smaller in one direction. In the helical wire 45a, the portion with the outside diameter which is constant serves as a constant wire-diameter portion 44, and the portion with the outside diameter which is progressively smaller in one direction as an increasing wire-diameter portion 41. The wire 45b has a constant outside diameter. The helical wire 45b (wire 421) serves as a constant wire-diameter portion 42.

In the coil 4B made up of the wires 45a, 45b, the wire portions 411, 421 of the increasing wire-diameter portion 41 and the constant wire-diameter portion 42 mesh with each other (enter each other's gaps) across the boundary between the increasing wire-diameter portion 41 and the constant wire-diameter portion 42. The region where the wires 411, 421 mesh with each other is referred to as a "biting region 451". The biting region 451 may also be referred to as a coupling region (wire coupling region) where the wires 411, 421 are coupled to each other.

Since the increasing wire-diameter portion 41 and the constant wire-diameter portion 42 overlap each other (in the biting region 451) across the boundary between the increasing wire-diameter portion 41 and the constant wire-diameter portion 42, the coupling strength of the boundary between the increasing wire-diameter portion 41 and the constant wire-diameter portion 42 is sufficiently maintained, and the rigidity varies gradually from the increasing wire-diameter portion 41 to the constant wire-diameter portion 42. As a result, the pliability of the guide wire 1 around the boundary (the biting region 451) between the increasing wire-diameter portion 41 and the constant wire-diameter portion 42 varies gradually with no stress concentration for increased kink resistance and safety.

With the guide wire 1B, the wire 45a (the increasing wire-diameter portion 41) and the wire 45b (the constant wire-diameter portion 42) may be made of the same material or different materials. If the wires 45a, 45b are made of the same material, then the kinds of the materials used become fewer, and the cost at which the guide wire 1B is manufactured is reduced. If the wires 45a, 45b are made of different materials, materials suitable for forming the increasing wire-diameter portion 41 (also the constant wire-diameter portion 45) and the constant wire-diameter portion 42 can be used.

The fixing material 52 should preferably not be disposed in the biting region 451. The rigidity from the constant wire-diameter portion 42 to the increasing wire-diameter portion 41 thus varies more gradually than if the fixing material 52 is disposed in the biting region 451.

Figure 6:
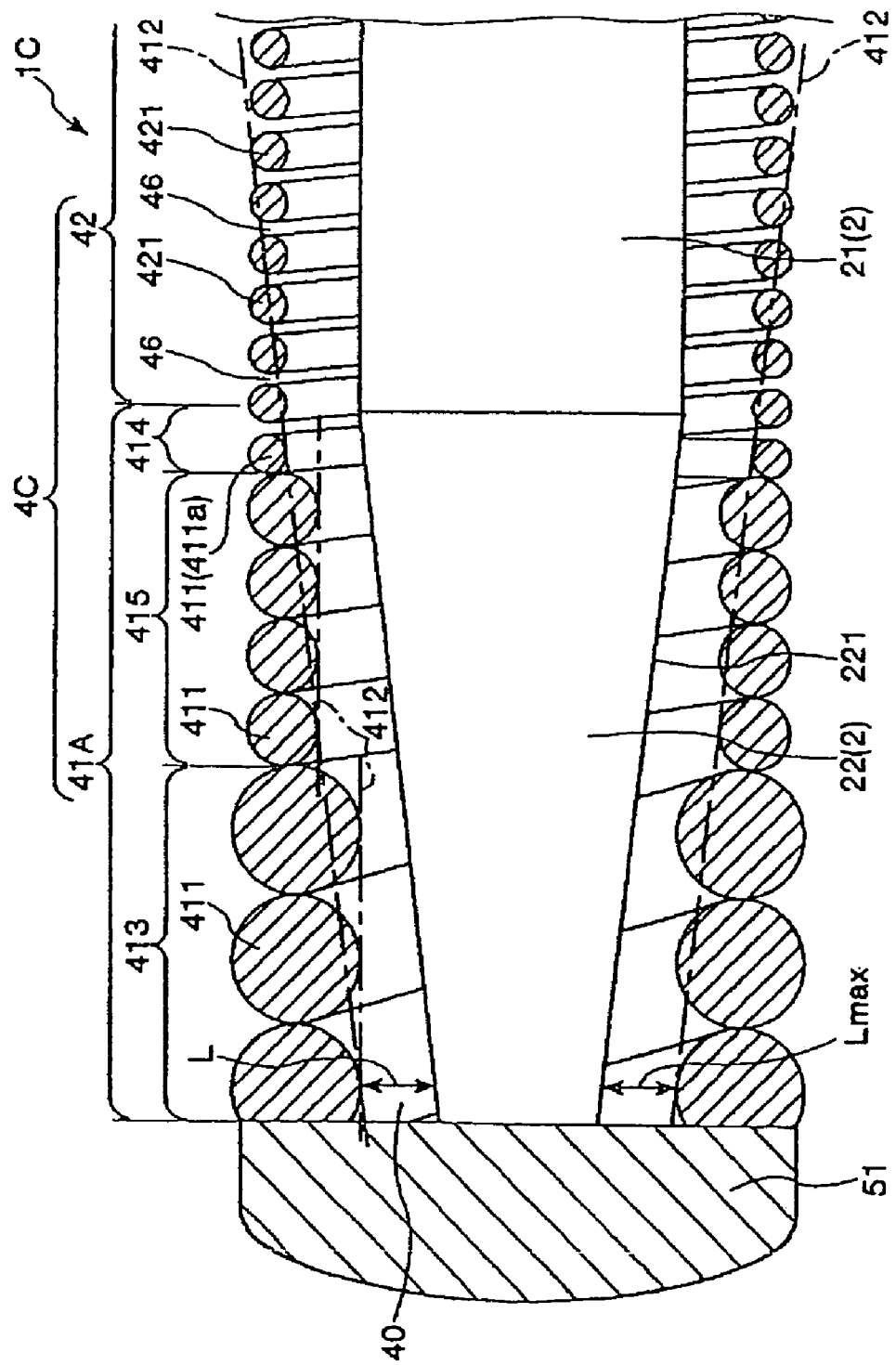
FIG. 6 is an enlarged detailed cross-sectional view showing a tapered portion of a guide wire according to a fourth embodiment of the present invention.

FIG. 6 illustrates a tapered portion of a guide wire according to a fourth embodiment. The description below of the guide wire according to this fourth embodiment will primarily address aspects of the guide wire different from those associated with the previously described embodiments. Features of the fourth embodiment similar to those in the previously described embodiments are identified by the same reference numeral and a detailed description of such features is not repeated.

The fourth embodiment is similar to the first embodiment except for the shape of the increasing wire-diameter portion. The coil 4C of the guide wire 1C shown in FIG. 6 has an increasing wire-diameter portion 41A including a wire 411 whose diameter increases stepwise toward the distal end. Specifically, the wire 411 includes a maximum-diameter portion 413 (at the distal end of the increasing wire-diameter portion 41A) where the diameter of the wire 411 is maximum, a minimum-diameter portion 414 which is disposed proximally of the maximum-diameter portion 413 (on the proximal end of the increasing wire-diameter portion 41A) where the diameter of the wire 411 is minimum, and an intermediate-diameter portion 415 which is disposed between the maximum-diameter portion 413 and the minimum-diameter portion 414 and where the diameter of the wire 411 is intermediate (i.e., the diameter of the wire 411 in the intermediate-diameter portion 415 is less than the diameter of the wire in the maximum-diameter portion 413 and greater than the diameter of the wire in the minimum-diameter portion 414).

In the increasing wire-diameter portion 41A, adjacent turns of the wire 411 are closely arranged with no gaps therebetween when no external forces are applied to the coil 4C.

In the coil 4C, the distance L of the clearance 40 is maximum (maximum distance $L_{max}$) at the distal end portion of the distal end portion of the maximum-diameter portion 413 (the most distal end portion of the increasing wire-diameter portion 41A). The distance L is smaller than the maximum distance $L_{max}$ in the portion of the coil 4C except for the maximum-diameter portion 413 (the intermediate-diameter portion 415 and the minimum-diameter portion 414). The size of the clearance 40 is thus minimized, making it more effective to prevent adjacent turns of the wire 411 (also the wire 421) from riding on one another when the guide wire 1C is pushed. Therefore, the guide wire 1C can be used in a normal state.

With the structure shown in FIG. 6, the diameter of the wire 411 of the increasing wire-diameter portion 41A varies in three steps. However, the diameter of the wire 411 is not limited to varying in three steps, but may vary in two steps or four or more steps.

The ratio of the wire diameters of the minimum-diameter portion 414, the intermediate-diameter portion 415, and the maximum-diameter portion 413 is not limited to any particular values, but should preferably in the range from 1:1.1 to 2:1.5 to 4 and more preferably in the range from 1:1.1 to 1.5:1.6 to 2.

Figure 7:
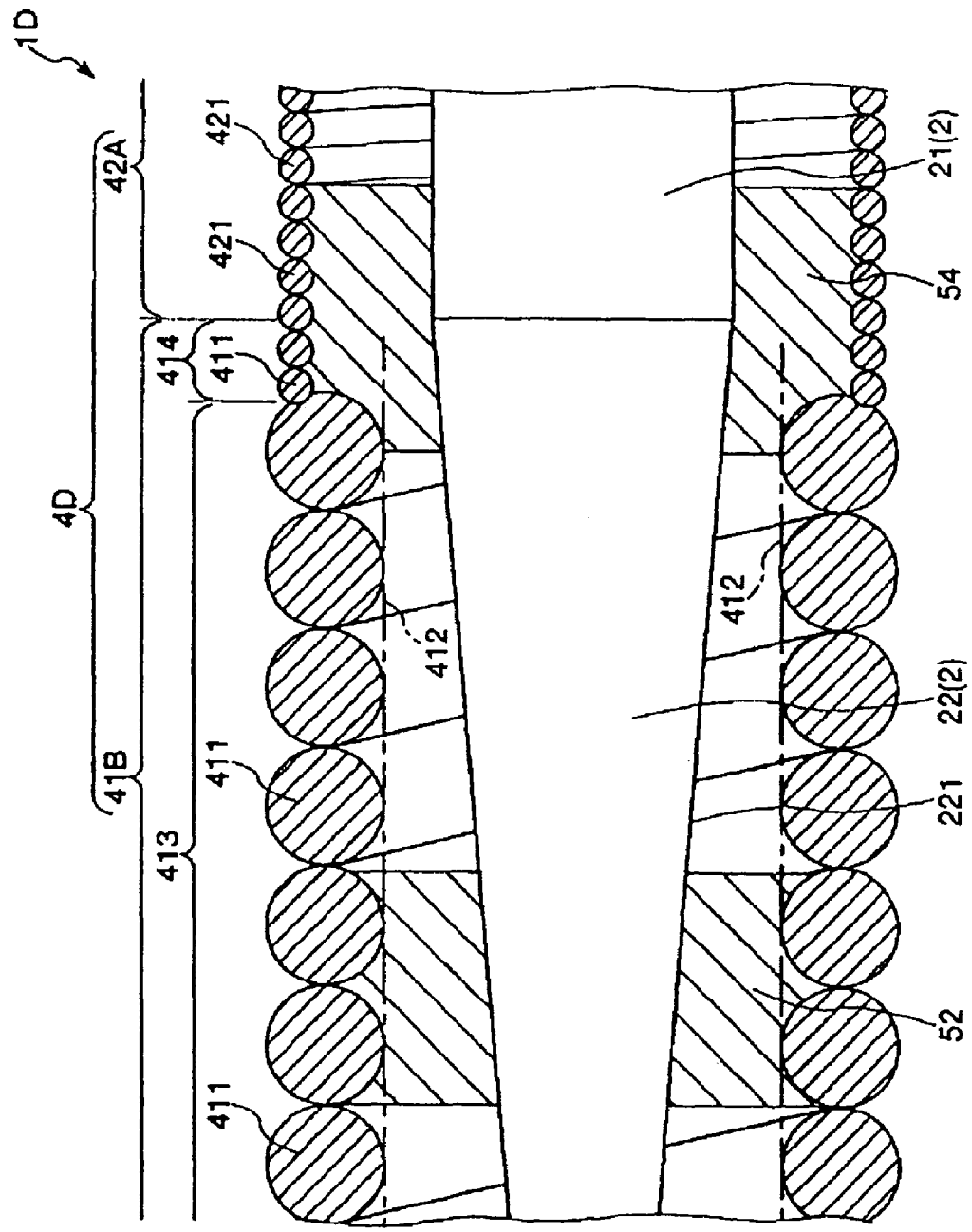
FIG. 7 is an enlarged detailed cross-sectional view showing a tapered portion of a guide wire according to a fifth embodiment of the present invention.

FIG. 7 illustrates a tapered portion of a guide wire according to a fifth embodiment. The description below of the guide wire according to this fifth embodiment will primarily address aspects of the guide wire different from those associated with the previously described embodiments. Features of the fifth embodiment similar to those in the previously described embodiments are identified by the same reference numeral and a detailed description of such features is not repeated.

This fifth embodiment is similar to the fourth embodiment except for the position where the fixed material is disposed. The coil 4D of the guide wire 1D shown in FIG. 7 does not include the intermediate-diameter portion 415. Therefore, an increasing wire-diameter portion 41B is made up of the maximum-diameter portion 413 and the minimum-diameter portion 414.

In a constant wire-diameter portion 42A, adjacent turns of a wire 421 are closely arranged with no gaps therebetween when no external forces are applied to the coil 4D.

The coil 4D is fixed to the wire body 10 at four locations. As with the coil 4 according to the first embodiment, two of the four locations are the distal end of the coil 4D (the increasing wire-diameter portion 41B) and the proximal end of the coil 4D (the constant wire-diameter portion 42A). The remaining two locations are the intermediate portion of the increasing wire-diameter portion 41B and the boundary between the increasing wire-diameter portion 41B and the constant wire-diameter portion 42A. The intermediate portion of the increasing wire-diameter portion 41B is fixed to an intermediate portion of the tapered portion 22 of the first wire 2 by a fixing material 52, and the boundary between the increasing wire-diameter portion 41B and the constant wire-diameter portion 42A is fixed to the boundary between the tapered portion 22 and the constant-diameter portion 21 by a fixing material 54.

By thus fixing the coil 4D at the above locations (four locations), the coil 4D can reliably be fixed in position without impairing the flexibility of the distal end portion of the guide wire 1D (where the coil 4D is present).

Figure 8:
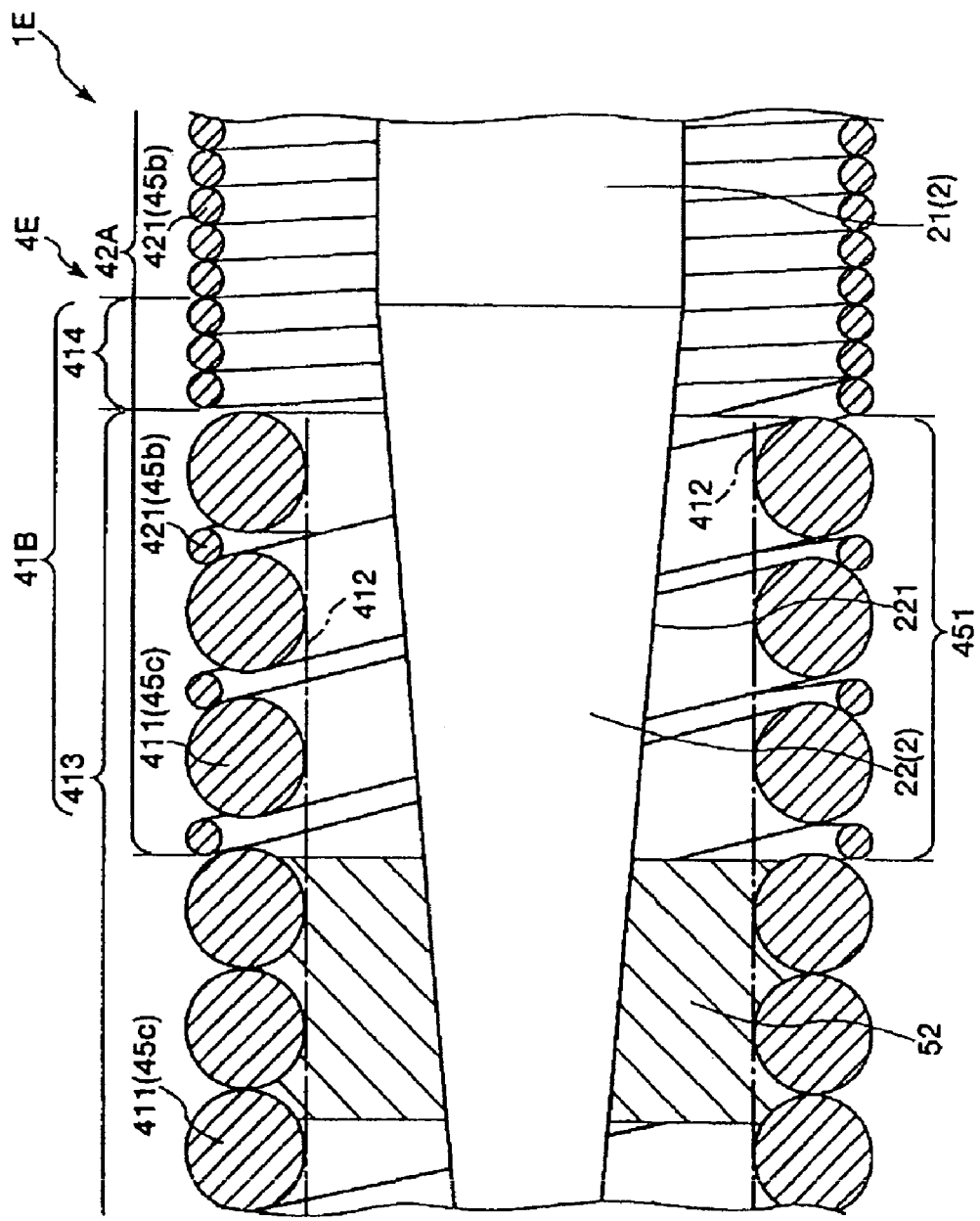
FIG. 8 is an enlarged detailed cross-sectional view showing a tapered portion of a guide wire according to a sixth embodiment of the present invention.

FIG. 8 illustrates a tapered portion of a guide wire according to a sixth embodiment. The description below of the guide wire according to this sixth embodiment will primarily address aspects of the guide wire different from those associated with the previously described embodiments. Features of the sixth embodiment similar to those in the previously described embodiments are identified by the same reference numeral and a detailed description of such features is not repeated.

This sixth embodiment is similar to the fifth embodiment except for the structure of the coil. The coil 4E of the guide wire 4E shown in FIG. 8 includes two individual wires 45c, 45b each helically wound. The wire 45c has a constant outside diameter. The helical wire 45c serves as a portion (a maximum-diameter portion 413) of the increasing wire-diameter portion 41B.

The wire 45b has a constant outside diameter which is smaller than the outside diameter of the wire 45c. The helical wire 45b (the wire 421) provides the constant outside-diameter portion 42 and the proximal end portion (the minimum-diameter portion 414) of the increasing wire-diameter portion 41B.

In the coil 4E constructed of the wires 45c, 45b, the boundary between the increasing wire-diameter portion 41B and the constant outside-diameter portion 42A serves as a biting portion 451 where the wires 411, 421 mesh with each other. The biting portion 451 gives a sufficient coupling strength between the increasing wire-diameter portion 41B and the constant wire-diameter portion 42A, and allows the rigidity to vary gradually from the constant wire-diameter portion 42A to the increasing wire-diameter portion 41B. As a result, the pliability of the guide wire 1E around the boundary (the biting region 451) between the increasing wire-diameter portion 41B and the constant wire-diameter portion 42A varies gradually with no significant stress concentration for increased kink resistance and safety.

The fixing material 52 should preferably not be disposed in the biting region 451. The rigidity from the constant wire-diameter portion 42A to the increasing wire-diameter portion 41B thus varies more gradually than if the fixing material 52 is disposed in the biting region 451.

Figure 9:
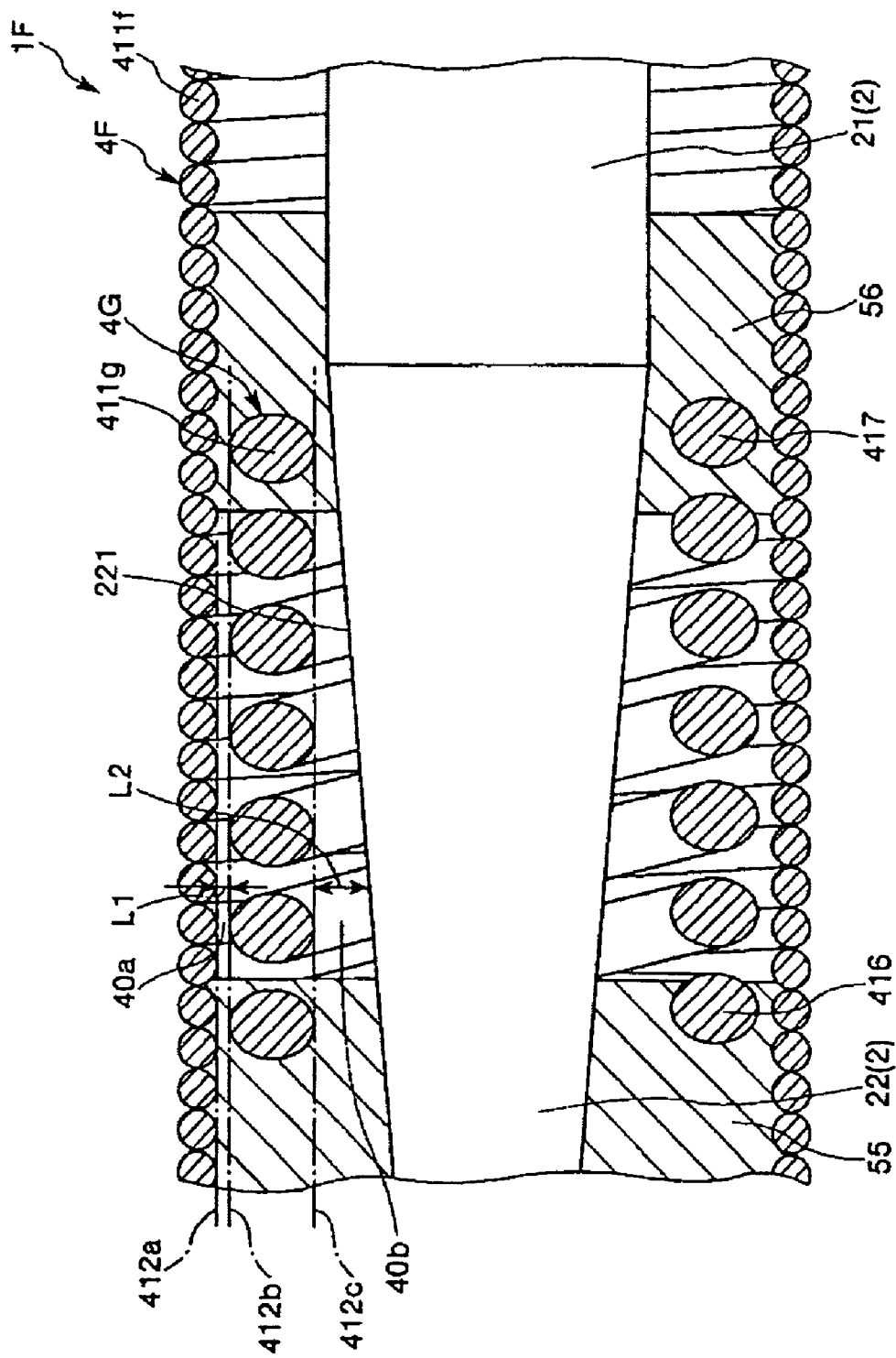
FIG. 9 is an enlarged detailed cross-sectional view showing a tapered portion of a guide wire according to a seventh embodiment of the present invention.

FIG. 9 illustrates a tapered portion of a guide wire according to a seventh embodiment. The description below of the guide wire according to this seventh embodiment will primarily address aspects of the guide wire different from those associated with the previously described embodiments. Features of the seventh embodiment similar to those in the previously described embodiments are identified by the same reference numeral and a detailed description of such features is not repeated.

The seventh embodiment is similar to the first embodiment except for the number of coils that are provided. The guide wire 1F shown in FIG. 9 has a helical first coil 4F disposed on the distal end portion of the wire body 10 and a helical second coil 4G disposed within the first coil 4F. Thus, the first coil 4F is positioned further radially outwardly than the second coil 4G.

The first coil 4F is disposed around the distal end portion of the wire body 10 in covering relation thereto. The first coil 4F includes a single first wire 411f having a circular cross-sectional area and helically shaped. The helical first coil 4F has an inside diameter which is constant along the longitudinal direction of the wire.

The second coil 4G is disposed within the first coil 4F. The second coil 4G includes a single second wire 411g having an elliptical cross-sectional area and helically shaped. The second wire 411g has a minor axis extending along the longitudinal direction of the wire.

In the guide wire 1F, the second coil 4G covers the outer circumference of the tapered portion 22 of the wire body 10 near the proximal end portion thereof, and the first coil 4F covers a range greater than the range of the second coil 4G. The clearance between the inner circumference of the first coil 4F and the outer circumference of the tapered portion 22 is reliably filled up with the second coil 4G. When the guide wire 1F is operated in a living body, vertical displacement in FIG. 9 of the first wire 411f of the first coil 4F is minimized to reliably prevent a turn of the first wire 411f from riding onto another adjacent turn when the guide wire 1F is pushed. The guide wire 1F can thus be used in a normal state, i.e., the pushing forces can be reliably transmitted to the distal end of the guide wire 1F.

A first clearance 40a is defined between the first coil 4F and the second coil 4G (i.e., between the inner surface of the first coil 4F and the outer surface of the second coil 4G), keeping the first coil 4F and the second coil 4G out of contact with each other. A second clearance 40b is defined between the second coil 4G and the wire body 10 (i.e., between the inner surface of the second coil 4G and the outer surface of the wire 2 or tapered portion 22), keeping the second coil 4g and the wire body 10 out of contact with each other.

Since these members are held out of contact with each other, they are liable to be deformed with ease when the guide wire 1F is operated in a living body, so that the operability of the guide wire 1F is increased. When the guide wire 1F is operated in a living body and its distal end portion is curved, the above members are prevented from developing friction therebetween. The members are thus made easily deformable for better operability of the guide wire 1F.

The distance L1 of the first clearance 40a (clearance distance) is constant along the longitudinal direction of the wire. The "distance L1" refers to the distance between a tangential line 412a that is tangential to the inner circumferential surface of the first coil 4F and a tangential line 412b that is tangential to the outer circumferential surface of the second coil 4G.

Since the distance L1 is constant, property changes of the guide wire 1F are smooth, any stress concentration on certain locations is reduced, and damage to the first coil 4F and the second coil 4G is reduced.

The distance L2 of the second clearance 40b (clearance distance) is progressively greater toward the distal end. The "distance L2" refers to the distance between a tangential line 412c that is tangential to the inner circumferential surface of the second coil 4G and the outer circumferential surface 221 of the tapered portion 22.

Since the distance L2 is progressively greater toward the distal end, even through the second coil 4G is disposed in an area corresponding to the tapered portion 22 of the guide wire 1F, the rigidity of the area of the guide wire 1F is gradually reduced toward the distal end. The distal end portion of the guide wire 1F is thus capable of well passing through constricted areas and is well pliable for an increased ability to follow blood vessels and increased safety, and is prevented from being bent over.

In the first coil 4F, adjacent turns of the first wire 411f are held in contact with each other in the absence of external forces. Therefore, the second wire 411g of the second coil 4G is reliably prevented from partly projecting from between the adjacent turns of the first wire 411f.

In the second coil 4G, adjacent turns of the second wire 411g are spaced from each other in the absence of external forces. Therefore, the portion of the guide wire 1F where the second coil 4G is provided is pliable to increase the operability of the guide wire 1F, i.e., to increase the ability to follow blood vessels and the safety.

The average diameter (the average value of major and minor diameters) of the second wire 411g, especially the average minor diameter, is greater than the average diameter of the first wire 411f. Therefore, the clearance between the inner circumference of the first coil 4F and the outer circumference of the tapered portion 22 is filled up with the second coil 4G as much as possible. Consequently, adjacent turns of the first wire 411f are reliably inhibited from riding onto one another.

The second coil 4G is fixed to the first wire 2 (wire body 10) at two locations. Specifically, the distal end 416 of the second coil 4G is fixed to the intermediate portion of the tapered portion 22 by a fixing material 55, and the proximal end 417 of the second coil 4G is fixed nearly to the boundary between the tapered portion 22 of the first wire 2 and the constant diameter portion 21 by a fixing material 56. By thus fixing the second coil 4G at the above locations, the pliability of the distal end portion of the guide wire 1F (where the second coil 4G is present) is inhibited from being impaired, and the second coil 4G is reliably fixed in position.

The fixing materials 55, 56 also serve to fix the first coil 4F to the second wire 2 (wire body 10). Specifically, the first coil 4F has an intermediate portion fixed by the fixing materials 55, 56 to the intermediate portion of the tapered portion 22 of the first wire 2 and nearly to the boundary between the tapered portion 22 and the constant diameter portion 21. Since the fixing materials 55, 56 also serve to fix the first coil 4F, fixing materials dedicated to fix only the first coil 4F are omitted, making the guide wire 1F relatively simple in construction.

The first coil 4F and the second coil 4G are not limited to any particular materials, but may be made of the same materials as the coil according to the first embodiment.

The diameter of the first wire 411f of the first coil 4F is not limited to being constant. The first coil 4F may include a portion where diameter of the first wire 411f varies.

In the illustrated arrangement, the second clearance 40b is progressively greater toward the distal end. However, the second clearance 40b may be constant along the longitudinal direction of the wire.

Figure 10:
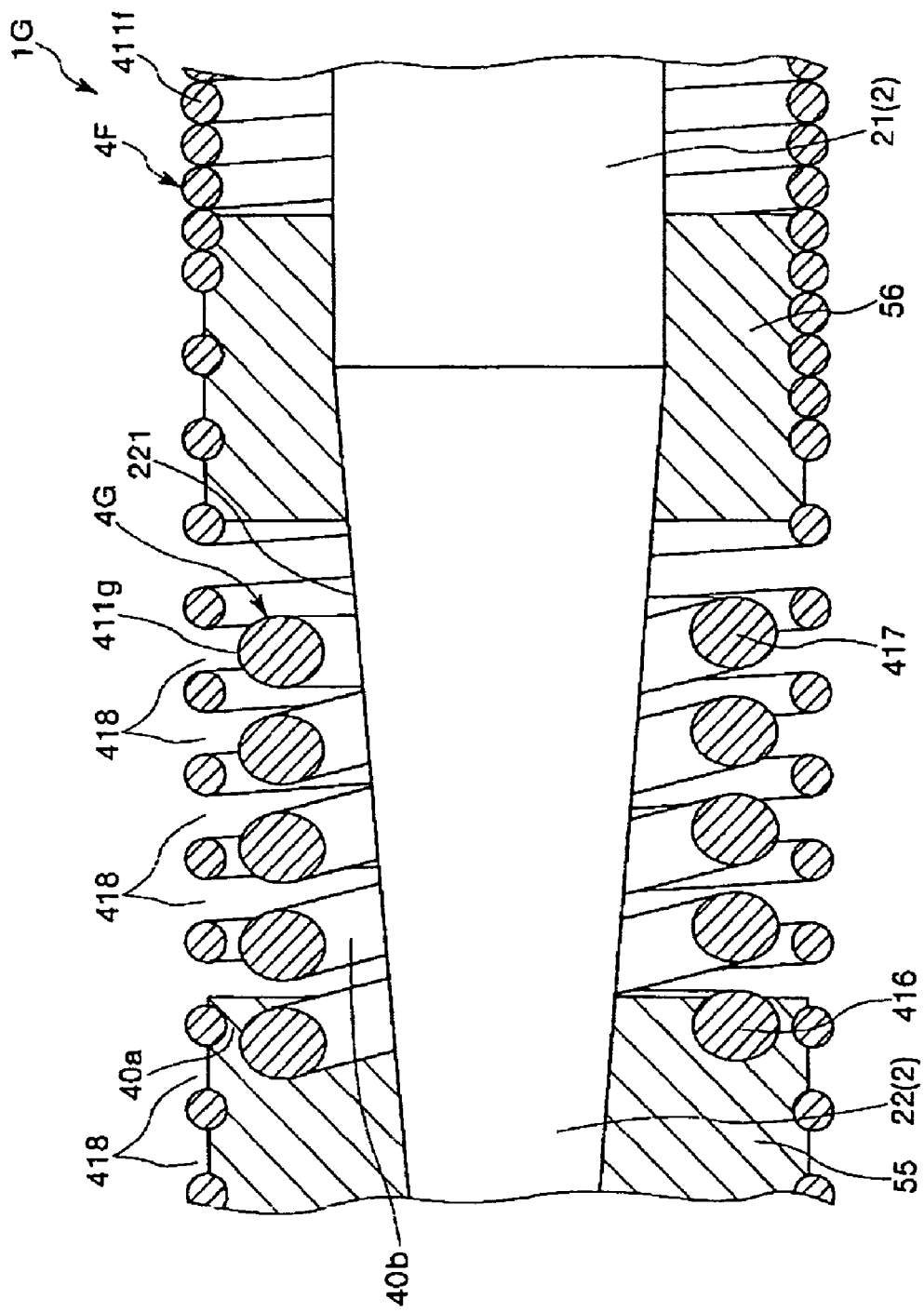
FIG. 10 is an enlarged detailed cross-sectional view showing a tapered portion of a guide wire according to a eight embodiment of the present invention.

FIG. 10 illustrates a tapered portion of a guide wire according to a eighth embodiment. The description below of the guide wire according to this eighth embodiment will primarily address aspects of the guide wire different from those associated with the previously described embodiments. Features of the eighth embodiment similar to those in the previously described embodiments are identified by the same reference numeral and a detailed description of such features is not repeated.

The eighth embodiment is similar to the seventh embodiment except for the manner in which the first coil is coiled and the manner in which the second coil is fixed to the wire body. The guide wire 1G shown in FIG. 10 has a first coil 4G wherein adjacent turns of the first wire 411f are spaced from each other in a portion extending from the boundary between the constant diameter portion 21 and the tapered portion 22 of the first wire 2 toward the distal end. Therefore, gaps 418 are defined between the adjacent turns of the first wire 411f. The portion of the first coil 4G where the gaps 418 are provided is pliable to increase the operability of the guide wire 1G.

The distances of the gaps 418 (the distance between adjacent turns of the first wire 411f are smaller than the minor diameter of the second wire 411g to prevent the second wire of the second coil 4G from partly projecting through the gaps 418.

In the guide wire 1G, the fixing material 56 serves to fix only the first coil 4F to the wire body 10, but not to fix the second coil 4G. The second coil 4G has a fixed distal end 416 and a free proximal end 417. By thus fixing the second coil 4G, the guide wire 1G is more pliable than if the proximal end 417 of the second coil 4G is fixed by the fixing material 56 (as in the seventh embodiment), and the rigidity of the guide wire 1G varies more gradually.

The guide wires disclosed here have been described above based on the illustrated embodiments. The present invention is not limited to the illustrated embodiments, as various parts of the guide wires may be replaced with other structures or features which can perform the same or similar functions. In addition, other structures or features may be added.

A guide wire may be constructed of a combination of a plurality of the structures or features described above in the above embodiments.

The principles, embodiments and modes of operation have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A guide wire comprising:
   a wire body having a tapered portion disposed on a distal end portion of the wire body and having an outside diameter progressively reduced toward a distal end of the taper portion, the tapered portion possessing an outer circumference;
   a coil disposed in covering relation to the distal end portion of the wire body and comprising a helically shaped wire possessing a diameter;
   wherein the helically shaped wire includes an increasing wire-diameter portion at which the diameter of the wire increases continuously in a direction toward a distal end of the increasing wire-diameter portion;
   the increasing wire-diameter portion being disposed in covering relation to the outer circumference of at least a portion of the tapered portion in a longitudinal direction; and
   the helically shaped wire comprising a constant wire-diameter portion where the diameter of the wire is constant, the constant wire-diameter portion being positioned adjacent to a proximal end of the increasing wire-diameter portion, the constant wire-diameter portion extending in a proximal direction from adjacent the proximal end of the increasing wire-diameter portion.

2. The guide wire according to claim 1, wherein the wire body and the coil are spaced from each other by a clearance distance which is substantially constant along a longitudinal direction of the wire body.

3. The guide wire according to claim 1, wherein adjacent turns of the wire of the increasing wire-diameter portion contact each other when no external force is applied to the guide wire.

4. The guide wire according to claim 1, wherein the coil possess an outside diameter which is constant along a longitudinal direction of the coil.

5. The guide wire according to claim 1, wherein the increasing wire-diameter portion possesses a minimum diameter at which the diameter of the wire is a minimum, the diameter of the constant wire-diameter portion being equal to or less than the minimum diameter of the increasing wire-diameter portion.

6. The guide wire according to claim 1, wherein the increasing wire-diameter portion and the constant wire-diameter portion together form a unitary, single, one-piece, wire.

7. The guide wire according to claim 1, wherein the increasing wire-diameter portion and the constant wire-diameter portion comprise two individual wires.

8. The guide wire according to claim 7, wherein a proximal end portion of the increasing wire-diameter portion and a distal end portion of the constant wire-diameter portion mesh with one another at a biting portion forming a boundary between the increasing wire-diameter portion and the constant wire-diameter portion.

9. The guide wire according to claim 8, comprising:
   a plurality of spaced apart fixing materials by which the coil is fixed to the wire body at a plurality of spaced apart locations; and
   wherein none of the fixing materials are disposed in the biting portion.

10. The guide wire according to claim 1, wherein the increasing wire-diameter portion and the constant wire-diameter portion are made of the same material.

11. The guide wire according to claim 1, wherein the increasing wire-diameter portion and the constant wire-diameter portion are made of different materials.

12. The guide wire according to claim 1, wherein adjacent turns of the wire of the increasing wire-diameter portion are spaced from each other so that gaps exist between adjacent turns of the increasing wire-diameter portion.

13. A guide wire comprising:
   a wire body having a tapered portion disposed on a distal end portion of the wire body and having an outside diameter progressively reduced toward a distal end of the taper portion, the tapered portion possessing an outer circumference;
   a coil disposed in covering relation to the distal end portion of the wire body and comprising a helically shaped wire possessing a diameter;
   the helically shaped wire including an increasing wire-diameter portion at which the diameter of the wire increases continuously from a proximal end of the increasing wire-diameter portion to a distal end of the increasing wire-diameter portion which is spaced from the proximal end of the increasing wire-diameter portion;
   the increasing wire-diameter portion covering the outer circumference of at least a portion of the tapered portion of the wire body in a longitudinal direction; and
   the helically shaped wire comprising a constant wire-diameter portion at which the diameter of the wire does not change from a distal end of the constant wire-diameter portion to a proximal end of the constant wire-diameter portion, the constant wire-diameter portion being positioned proximally of the increasing wire-diameter portion so that the distal end of the constant wire-diameter portion is positioned proximally of the distal end of the increasing wire-diameter portion.

14. The guide wire according to claim 13, wherein the wire body and the coil are spaced from each other by a clearance distance so that a space exists between an outer surface of the wire body and an inner surface of the coil.

15. The guide wire according to claim 13, wherein adjacent turns of the wire of the increasing wire-diameter portion contact each other in absence of an external force applied to the guide wire.

16. The guide wire according to claim 13, wherein the increasing wire-diameter portion of the coil possess an outside diameter which is constant along a longitudinal direction of the increasing wire-diameter portion.

17. The guide wire according to claim 13, wherein the increasing wire-diameter portion possesses a minimum diameter at which the diameter of the wire is a minimum, the diameter of the constant wire-diameter portion being equal to or less than the minimum diameter of the increasing wire-diameter portion.

18. The guide wire according to claim 13, wherein the coil possesses a distal-most end and a proximal-most end, and the increasing wire-diameter portion possesses a distal-most end and a proximal-most end, the distal-most end of the increasing wire-diameter portion being located at the distal-most end of the coil.

19. A guide wire comprising:
a wire body having a tapered portion disposed on a distal end portion of the wire body and having an outside diameter progressively reduced toward a distal end of the taper portion, the tapered portion possessing an outer circumference;
a coil disposed in covering relation to the distal end portion of the wire body and comprising a helically shaped wire possessing a diameter;
the helically shaped wire including an increasing wire-diameter portion at which the diameter of the wire increases continuously from a proximal end of the increasing wire-diameter portion to a distal end of the increasing wire-diameter portion;
the increasing wire-diameter portion covering the outer circumference of at least a portion of the tapered portion of the wire body in a longitudinal direction; and
the helically-shaped wire comprising a constant wire-diameter portion at which the diameter of the wire does not change from a distal end of the constant wire-diameter portion to a proximal end of the constant wire-diameter portion, the constant wire-diameter portion being positioned proximally of the increasing wire-diameter portion;
the wire in the increasing wire-diameter portion possessing a minimum diameter at which the diameter of the wire is a smallest diameter, the diameter of the wire in the constant wire-diameter portion being equal to or less than said smallest diameter of the wire in the increasing wire-diameter portion.

20. The guide wire according to claim 19, wherein the wire body and the coil are spaced from each other by a clearance distance so that a space exists between an outer surface of the wire body and an inner surface of the coil.

21. The guide wire according to claim 19, wherein adjacent turns of the wire of the increasing wire-diameter portion contact each other in absence of an external force applied to the guide wire.

22. The guide wire according to claim 19, wherein the increasing wire-diameter portion of the coil possess an outside diameter which is constant along a longitudinal direction of the increasing wire-diameter portion.

23. The guide wire according to claim 19, wherein the increasing wire-diameter portion possesses a minimum diameter at which the diameter of the wire is a minimum, the diameter of the constant wire-diameter portion being equal to or less than the minimum diameter of the increasing wire-diameter portion.

* * * * *